(12) United States Patent
Yanez, Jr. et al.

(10) Patent No.: US 10,730,715 B2
(45) Date of Patent: *Aug. 4, 2020

(54) APPARATUS AND METHOD FOR ISOLATING A BROKEN ELASTIC STRAND

(71) Applicant: The Procter & Gamble Company, Cincinnati, OH (US)

(72) Inventors: Ricky Reynaldo Yanez, Jr., Cincinnati, OH (US); Nicholas Paul Goyette, Cincinnati, OH (US); Tina Brown, Cincinnati, OH (US); Gregory Hugh Dean, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/734,463

(22) Filed: Jan. 6, 2020

(65) Prior Publication Data
US 2020/0140224 A1 May 7, 2020

Related U.S. Application Data

(62) Division of application No. 15/644,932, filed on Jul. 10, 2017, now Pat. No. 10,556,770, which is a
(Continued)

(51) Int. Cl.
*B65H 54/00* (2006.01)
*A61F 13/49* (2006.01)
*A61F 13/15* (2006.01)

(52) U.S. Cl.
CPC ....... *B65H 54/00* (2013.01); *A61F 13/15593* (2013.01); *A61F 13/15772* (2013.01); *A61F 13/15804* (2013.01); *A61F 13/49009* (2013.01)

(58) Field of Classification Search
CPC ............... B65H 54/00; A61F 13/15593; A61F 13/15772; A61F 13/15804; A61F 13/49009
See application file for complete search history.

(56) References Cited

U.S. PATENT DOCUMENTS

| | | |
|---|---|---|
| 3,860,003 A | 1/1975 | Buell |
| 4,610,678 A | 9/1986 | Weisman et al. |
| (Continued) | | |

FOREIGN PATENT DOCUMENTS

| | | |
|---|---|---|
| EP | 1410778 A2 | 4/2004 |
| WO | WO 2014120561 A1 | 8/2014 |
| (Continued) | | |

OTHER PUBLICATIONS

PCT International Search Report, dated Jan. 8, 2015, 10 pages.
All Office Actions, U.S. Appl. No. 14/492,152.
All Office Actions, U.S. Appl. No. 15/644,932.

*Primary Examiner* — Vishal I Patel
(74) *Attorney, Agent, or Firm* — C. Brant Cook

(57) ABSTRACT

The present disclosure relates to manufacturing elastomeric laminates that may include a first substrate, a second substrate, and an elastic material located between the first substrate and second substrate. Methods and apparatuses may be configured to automatically isolate elastic strands that may break during the assembly process. As discussed in more detail below, the apparatuses may include a snare member extending adjacent to and across a travel path of elastic materials in a converting process. Thus, during the manufacture process, stretched elastics strands may advance past the snare member without contacting the outer circumferential surface of the snare member before being joined with a substrate. In the event that an elastic strand breaks, an upstream end portion of the elastic strand may retract back toward the snare member, wherein the upstream end portion (Continued)

wraps partially or completely around the outer circumferential surface of the snare member.

6 Claims, 8 Drawing Sheets

Related U.S. Application Data division of application No. 14/492,152, filed on Sep. 22, 2014, now Pat. No. 9,758,339.

(60) Provisional application No. 61/883,388, filed on Sep. 27, 2013.

(56) References Cited

U.S. PATENT DOCUMENTS

| | | | |
|---|---|---|---|
| 4,673,402 A | 6/1987 | Weisman et al. |
| 4,695,278 A | 9/1987 | Lawson |
| 4,704,115 A | 11/1987 | Buell |
| 4,795,454 A | 1/1989 | Dragoo |
| 4,834,735 A | 5/1989 | Alemany et al. |
| 4,888,231 A | 12/1989 | Angstadt |
| 4,909,803 A | 3/1990 | Aziz et al. |
| 5,167,897 A | 12/1992 | Weber et al. |
| 5,360,420 A | 11/1994 | Cook et al. |
| 5,562,646 A | 10/1996 | Goldman et al. |
| 5,599,335 A | 2/1997 | Goldman et al. |
| 5,628,097 A | 5/1997 | Benson et al. |
| 5,643,588 A | 7/1997 | Roe et al. |
| 5,669,894 A | 9/1997 | Goldman et al. |
| 5,674,216 A | 10/1997 | Buell et al. |
| 5,702,551 A | 12/1997 | Huber et al. |
| 5,916,661 A | 6/1999 | Benson et al. |
| 5,968,025 A | 10/1999 | Roe et al. |
| 6,107,537 A | 8/2000 | Elder et al. |
| 6,107,539 A | 8/2000 | Palumbo et al. |
| 6,118,041 A | 9/2000 | Roe et al. |
| 6,153,209 A | 11/2000 | Vega et al. |
| 6,410,129 B2 | 6/2002 | Zhang et al. |
| 6,426,444 B2 | 7/2002 | Roe et al. |
| 6,545,197 B1 | 4/2003 | Muller et al. |
| 6,586,652 B1 | 7/2003 | Roe et al. |
| 6,617,016 B2 | 9/2003 | Zhang et al. |
| 6,627,787 B1 | 9/2003 | Roe et al. |
| 6,790,798 B1 | 9/2004 | Suzuki et al. |
| 6,825,393 B2 | 11/2004 | Roe et al. |
| 6,861,571 B1 | 3/2005 | Roe et al. |
| 7,569,039 B2 | 8/2009 | Matsuda et al. |
| 2004/0097895 A1 | 5/2004 | Busam et al. |
| 2004/0158212 A1 | 8/2004 | Ponomarekno et al. |
| 2005/0107764 A1 | 5/2005 | Matsuda et al. |
| 2007/0131343 A1 | 6/2007 | Nordang |
| 2007/0219521 A1 | 9/2007 | Hird et al. |
| 2009/0312730 A1 | 12/2009 | LaVon et al. |
| 2011/0139657 A1 | 6/2011 | Hird et al. |
| 2011/0139658 A1 | 6/2011 | Hird et al. |
| 2011/0139659 A1 | 6/2011 | Hird et al. |
| 2011/0139662 A1 | 6/2011 | Hird et al. |
| 2011/0152812 A1 | 6/2011 | Hird et al. |
| 2012/0061015 A1 | 3/2012 | LaVon et al. |
| 2012/0061016 A1 | 3/2012 | LaVon et al. |
| 2013/0199696 A1 | 8/2013 | Schneider et al. |
| 2013/0199707 A1 | 8/2013 | Schneider et al. |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0277154 A1 | 10/2013 | Fritz et al. |
| 2014/0209652 A1 | 8/2014 | Smith |
| 2014/0224855 A1 | 8/2014 | Smith |

FOREIGN PATENT DOCUMENTS

| | | | | |
|---|---|---|---|---|
| WO | WO-2014126693 A1 * | 8/2014 | ....... | A61F 13/49009 |
| WO | WO 2014126693 A1 | 8/2014 | | |

* cited by examiner

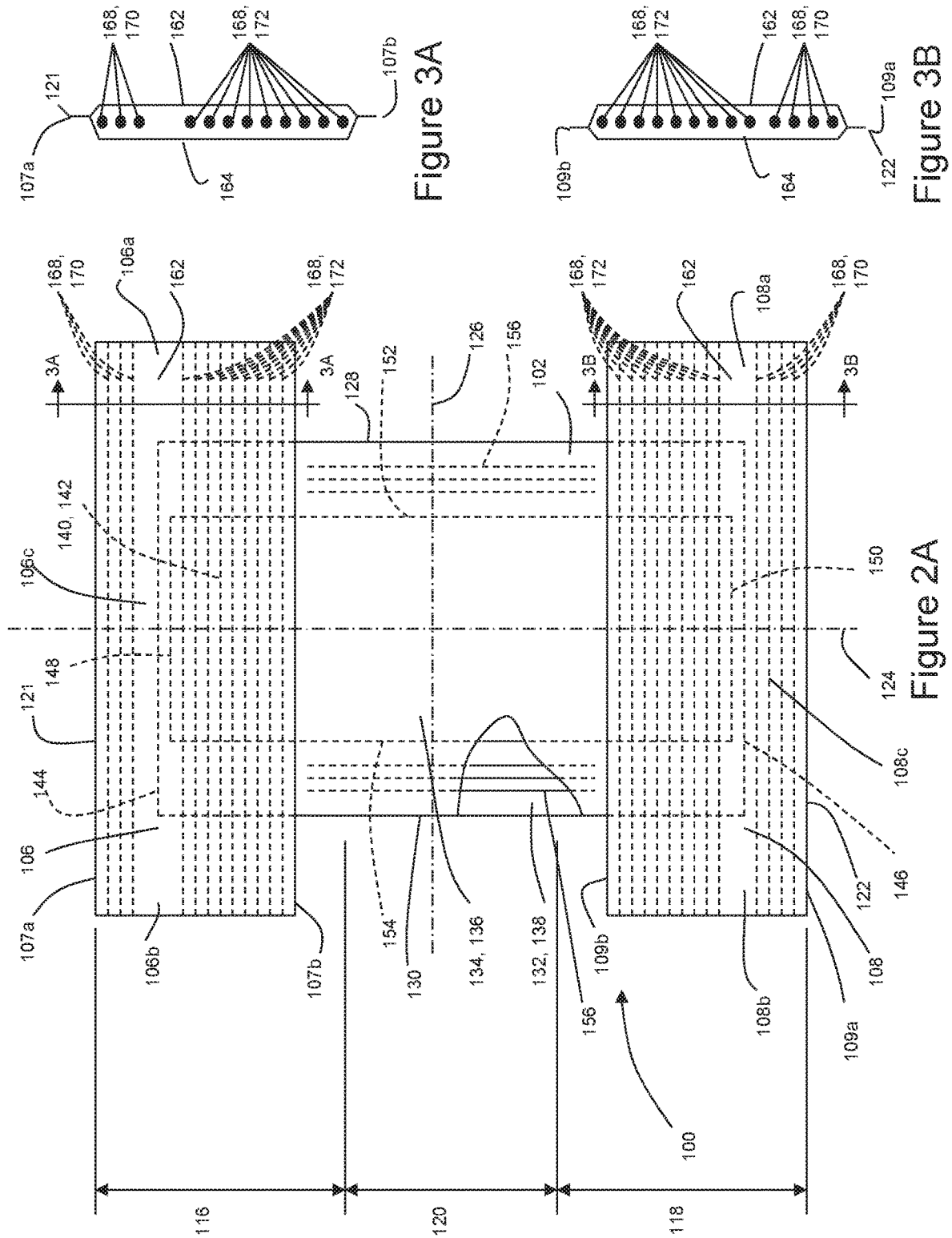

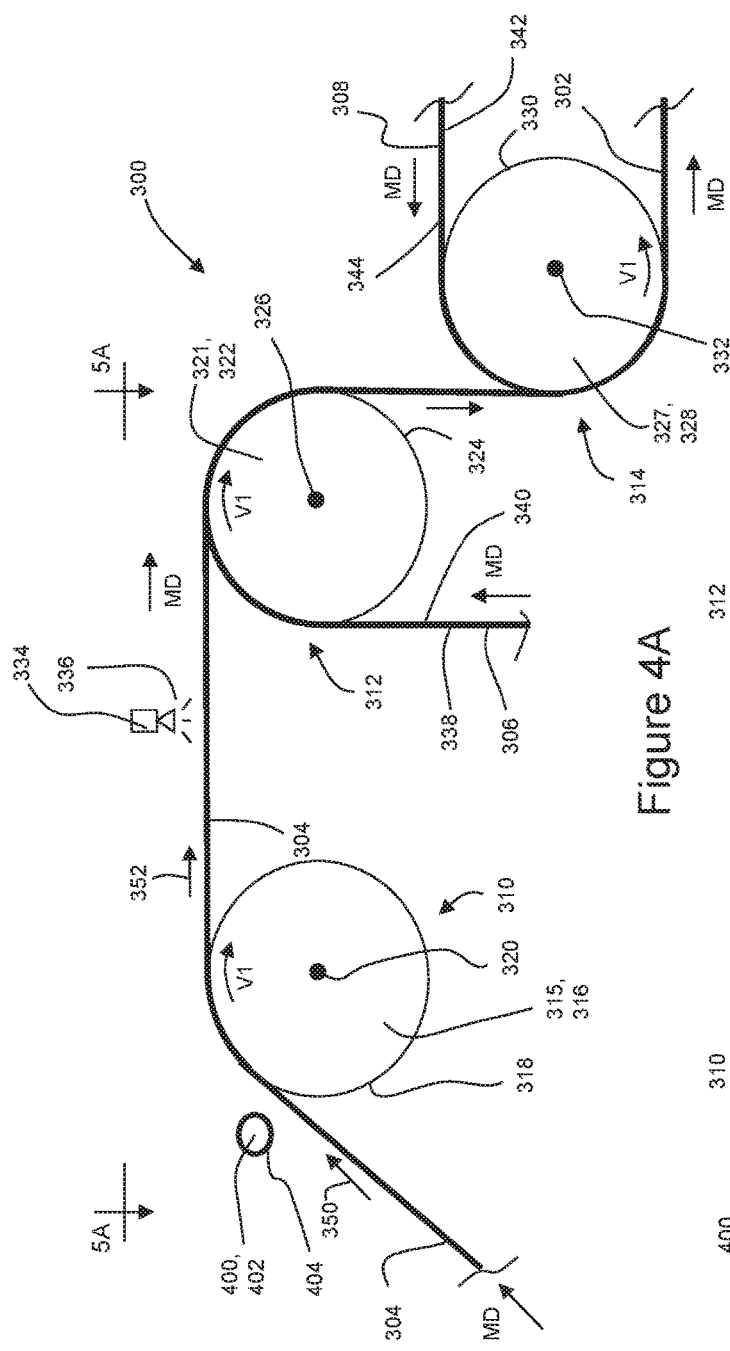
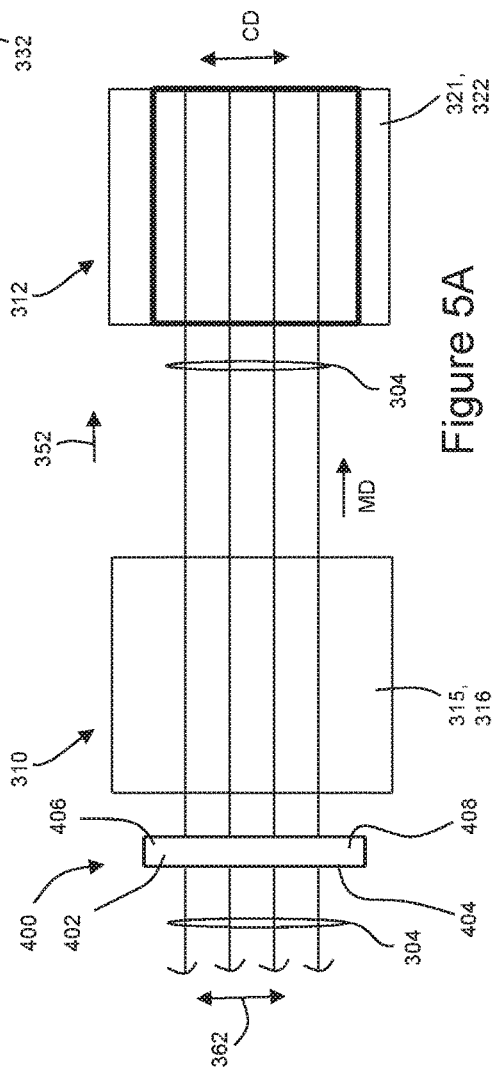
Figure 4A
Figure 5A

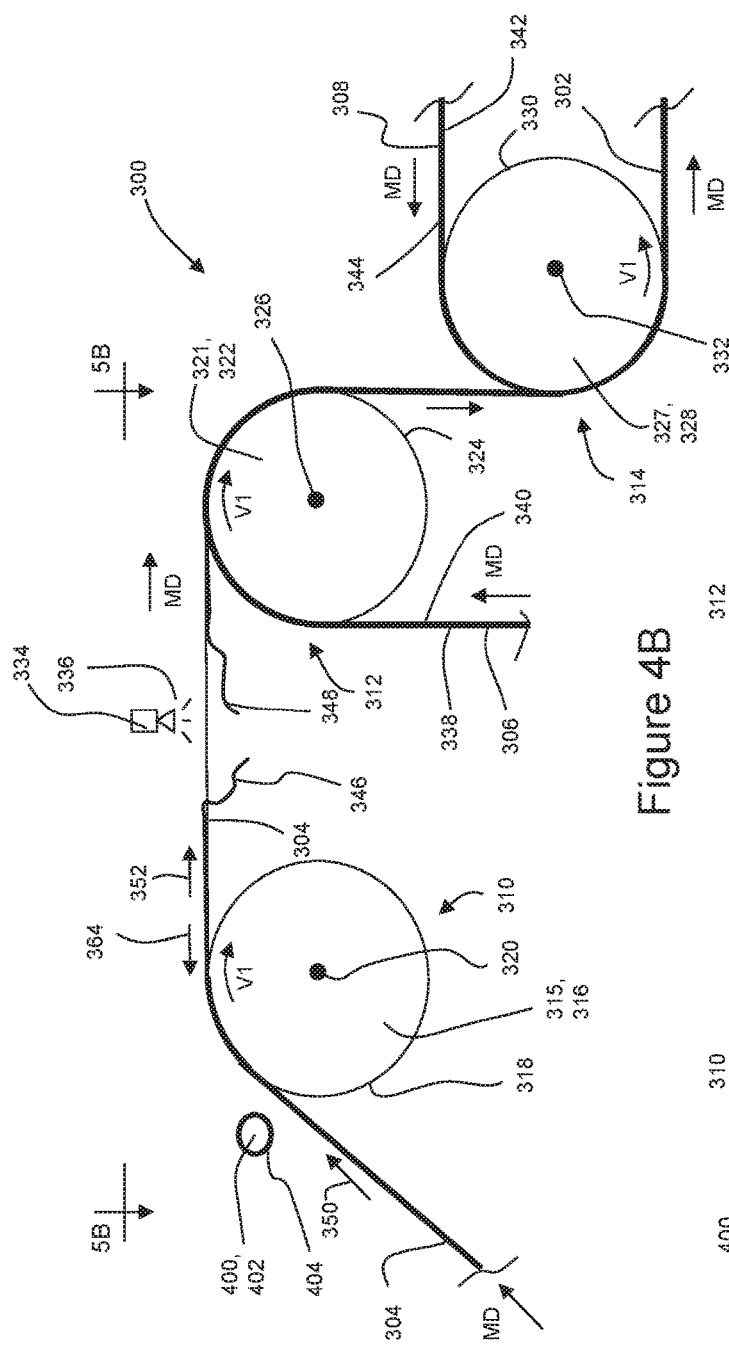
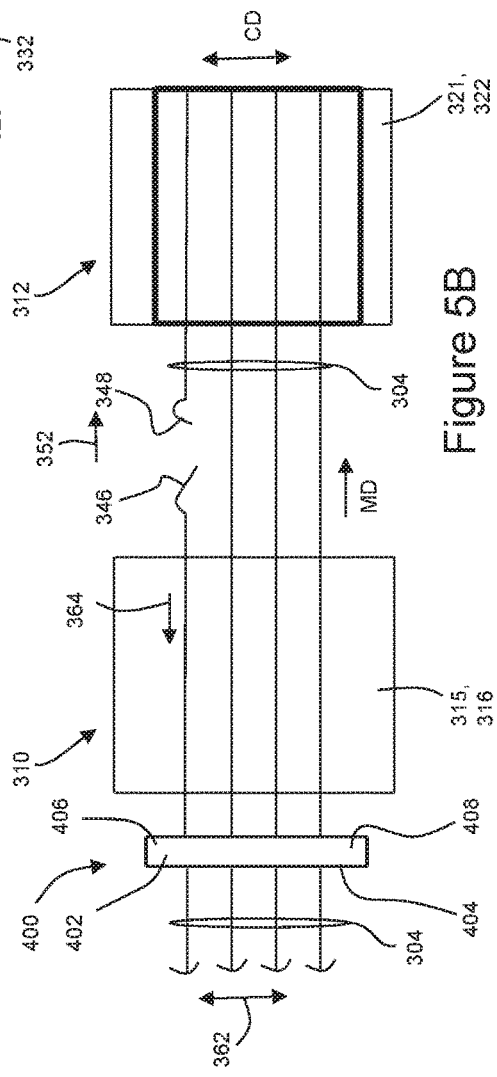
Figure 4B
Figure 5B

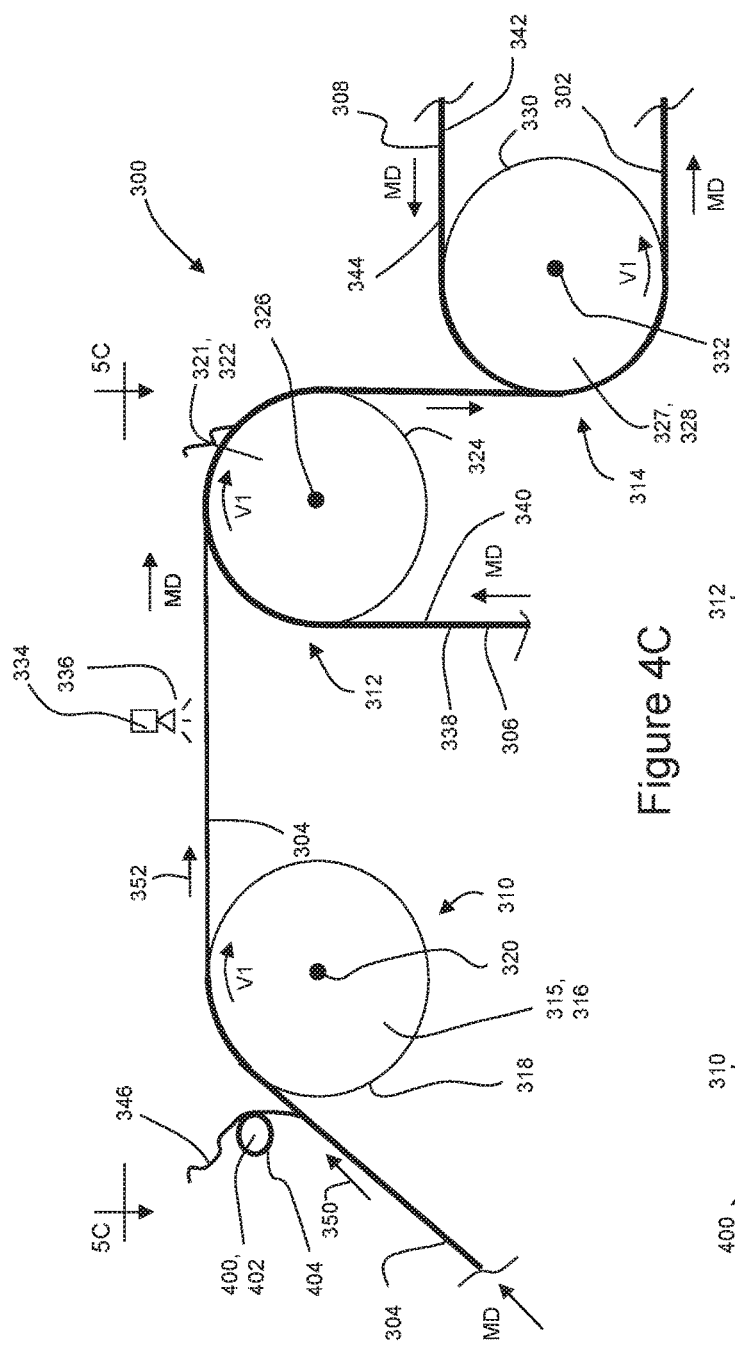
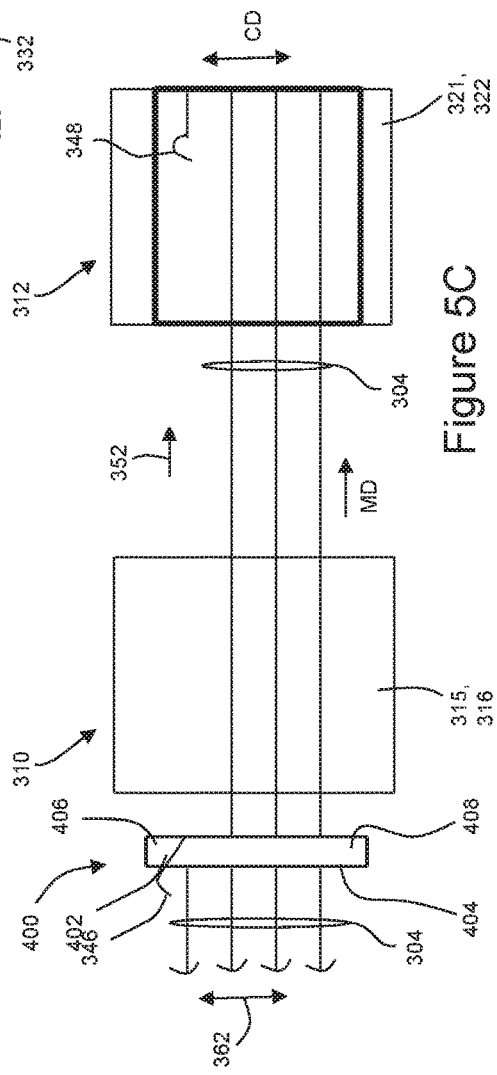
Figure 4C
Figure 5C

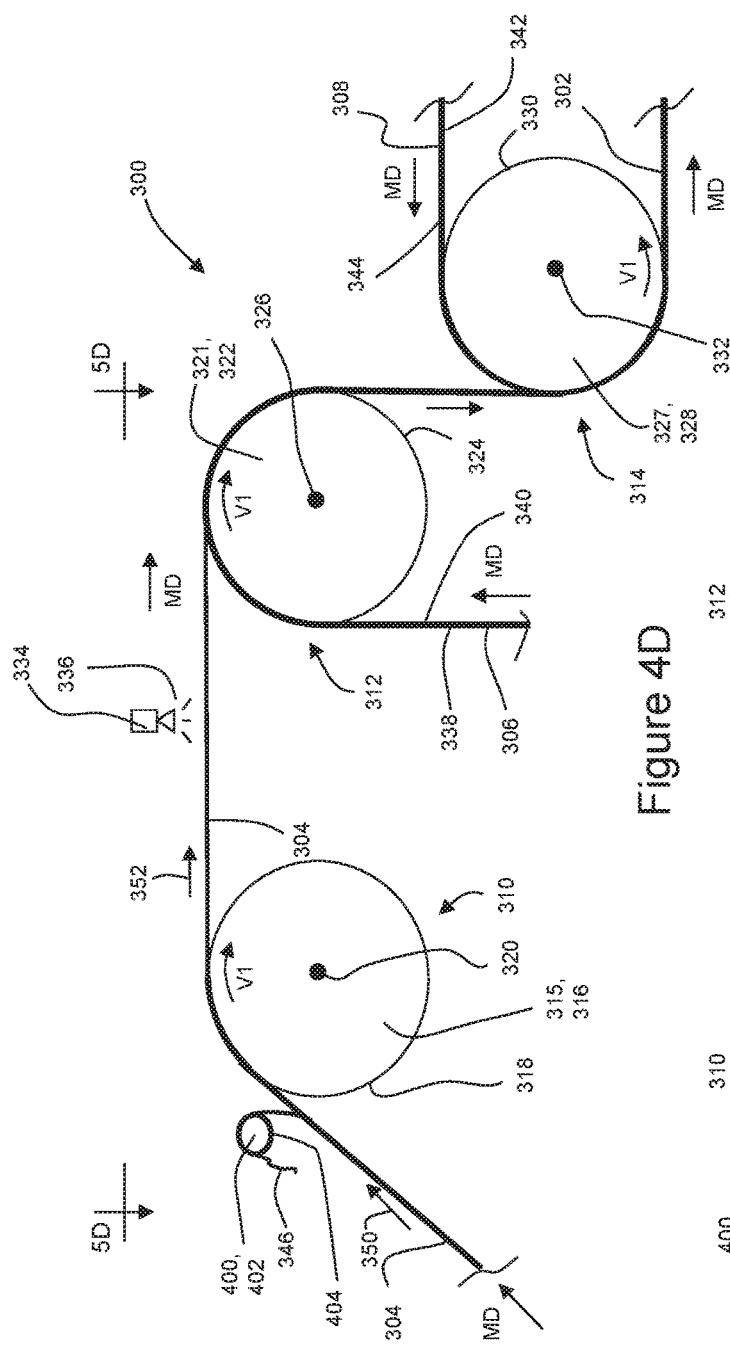
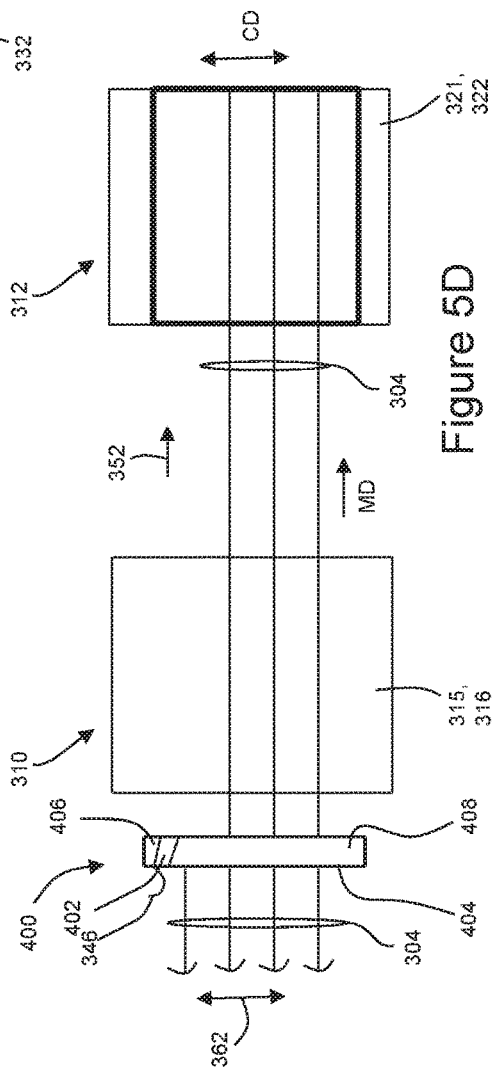
Figure 4D
Figure 5D

APPARATUS AND METHOD FOR ISOLATING A BROKEN ELASTIC STRAND

CROSS REFERENCE TO RELATED APPLICATIONS

This application is a divisional of U.S. patent application Ser. No. 15/644,932, filed on Jul. 10, 2017, which is a divisional of U.S. patent application Ser. No. 14/492,152, filed on Sep. 22, 2014, now U.S. Pat. No. 9,758,339, which claims the benefit of U.S. Provisional Application No. 61/883,388, filed on Sep. 27, 2013, all of which are incorporated by reference herein.

FIELD OF THE INVENTION

The present disclosure relates to methods for manufacturing absorbent articles, and more particularly, to apparatuses and methods for making elastomeric laminates that may be used as components of absorbent articles.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from an advancing web or webs are combined with other individual components created from other advancing webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

Some absorbent articles have components that include elastomeric laminates. Such elastomeric laminates may include an elastic material bonded to one or more nonwovens. The elastic material may include an elastic film and/or elastic strands. In some laminates, a plurality of elastic strands are joined to a nonwoven while the plurality of strands are in a stretched condition so that when the elastic strands relax, the nonwoven gathers between the locations where the nonwoven is bonded to the elastic strands forming corrugations. The resulting elastomeric laminate is stretchable to the extent that the corrugations allow the elastic strands to elongate.

During the manufacture of elastic laminates, problems can be encountered in the manufacturing process when bonding elastic strands to substrates. For example, tensioned elastic strands may break during the assembly process. If a strand breaks under tension, a loose end of the broken strand may tend to snap back a significant distance toward an upstream portion of the manufacturing process. As such, the loose end may become entangled in other upstream manufacturing components, which in turn, may necessitate stopping the process in order to properly rethread the elastic strand to the intended position on the production machinery. In some configurations, several strands may advance through a manufacture process in close proximity to one another. Thus, a violent and uncontrolled retraction of a loose end of a broken strand may also cause additional strands to become broken. Consequently, it would be beneficial to provide a method and apparatus for producing an elastomeric laminate that is capable of automatically capturing and isolating upstream end portions of elastic strands that break during the production process to help reduce the amount of rethreading that would otherwise be necessary and to help reduce the likelihood of causing adjacent elastic strands in the process to become broken. Such methods and apparatus may also be used as a troubleshooting device to help identify the specific locations along the assembly line where elastic strands are breaking. It would also be beneficial to provide such a device that is positioned adjacent the travel path of the elastic strands without the need to thread elastic strands through the device and/or have the elastic strands contact the device.

SUMMARY OF THE INVENTION

The present disclosure relates to making elastomeric laminates that may include a first substrate, a second substrate, and an elastic material located between the first substrate and second substrate. Methods and apparatuses may be configured to automatically isolate elastic strands that may break during the assembly process. As discussed in more detail below, the apparatuses may include a snare member extending adjacent to and across a travel path of elastic materials in a converting process. Thus, during the manufacture process, stretched elastics strands may advance past the snare member without contacting the outer circumferential surface of the snare member before being joined with a substrate. In the event that an elastic strand breaks, an upstream end portion of the elastic strand may retract back toward the snare member, wherein the upstream end portion wraps partially or completely around the outer circumferential surface of the snare member.

In one form, a method for isolating broken strands of elastic includes the steps of: advancing a plurality of elastic strands in a first direction to a drum and defining a first strand transport plane; wrapping the plurality of elastic strands along an outer circumferential surface of the drum; advancing the plurality of elastic strands from the outer circumferential surface of the drum in a second direction and defining a second strand transport plane; positioning a snare member adjacent the drum, wherein the snare member has an outer circumferential surface and a defines a length defined between a first end portion and a second end portion, wherein the length of the snare member extends in a third direction across the plurality of elastic strands, and wherein the outer circumferential surface of the snare member is positioned between the plurality of elastic strands and the strand transport plane; separating an elastic strand in the second direction to create an upstream end portion and a downstream end portion; retracting the upstream end portion toward the drum; unwrapping the upstream end portion from the outer circumferential surface of the drum; and wrapping the upstream end portion along the outer circumferential surface of the snare member.

In another form, a method for isolating broken strands of elastic includes the steps of: advancing an elastic strand in a first direction to a first tangent point on an outer circumferential surface of a drum; wrapping the elastic strand along the outer circumferential surface of the drum, wherein the elastic strand extends from the first tangent point to a second tangent point on the outer circumferential surface of the drum; advancing the elastic strand from the second tangent point on the outer circumferential surface of the drum in a second direction; positioning a snare member adjacent the drum, wherein the snare member has an outer circumferential surface and defines a length defined between a first end portion and a second end portion, wherein the length of the snare member extends in a third direction across the first direction of advancement of the elastic strand, and wherein the snare member is positioned between the elastic strand and a plane extending through the second tangent point; separating the elastic strand in the second direction to create an upstream end portion and a downstream end portion; retracting the upstream end portion toward the drum; and wrapping the upstream end portion along the outer circumferential surface of the snare member.

In yet another form, a method for isolating broken strands of elastic includes the steps of: advancing an elastic strand in a first direction to a first tangent point on an outer circumferential surface of a drum; wrapping the elastic strand along the outer circumferential surface of the drum, wherein a wrapped length of the elastic strand extends from the first tangent point to a second tangent point on the outer circumferential surface of the drum; advancing the elastic strand from the second tangent point on the outer circumferential surface of the drum in a second direction; positioning a snare member adjacent the drum, wherein the snare member has an outer circumferential surface and defines a length defined between a first end portion and a second end portion, wherein the length of the snare member extends in a third direction across the first direction of advancement of the elastic strand, wherein the snare member is positioned between a first plane extending through the first tangent point and a second plane extending through the second tangent point; separating the elastic strand in the second direction to create an upstream end portion and a downstream end portion; retracting the upstream end portion toward the drum; unwrapping the upstream end portion from the outer circumferential surface of the drum; and wrapping the upstream end portion along the outer circumferential surface of the snare member.

BRIEF DESCRIPTION OF THE DRAWINGS

FIG. 2A is a partially cut away plan view of the diaper pant shown in FIG. 1.

FIG. 3A is a cross-sectional view of the diaper pants of FIGS. 2A and 2B taken along line 3A-3A.

FIG. 3B is a cross-sectional view of the diaper pants of FIGS. 2A and 2B taken along line 3B-3B.

FIG. 4A is a schematic side view of a converting apparatus adapted to manufacture an elastic laminate including a first substrate, a second substrate, and elastic strands.

FIG. 4B is a schematic side view of the converting apparatus shown in FIG. 4A showing a broken elastic strand.

FIG. 4C is a schematic side view of the converting apparatus shown in FIG. 4B showing an upstream end portion of the broken elastic strand contacting an outer circumferential surface of a snare member.

FIG. 4D is a schematic side view of the converting apparatus shown in FIG. 4C showing an upstream end portion of the broken elastic strand captured by a snare member.

FIG. 5A is a view of the converting apparatus shown in FIG. 4A taken along line 5A-5A.

FIG. 5B is a view of the converting apparatus shown in FIG. 4B taken along line 5B-5B.

FIG. 5C is a view of the converting apparatus shown in FIG. 4C taken along line 5C-5C.

FIG. 5D is a view of the converting apparatus shown in FIG. 4D taken along line 5D-5D.

DETAILED DESCRIPTION OF THE INVENTION

Figure 1:
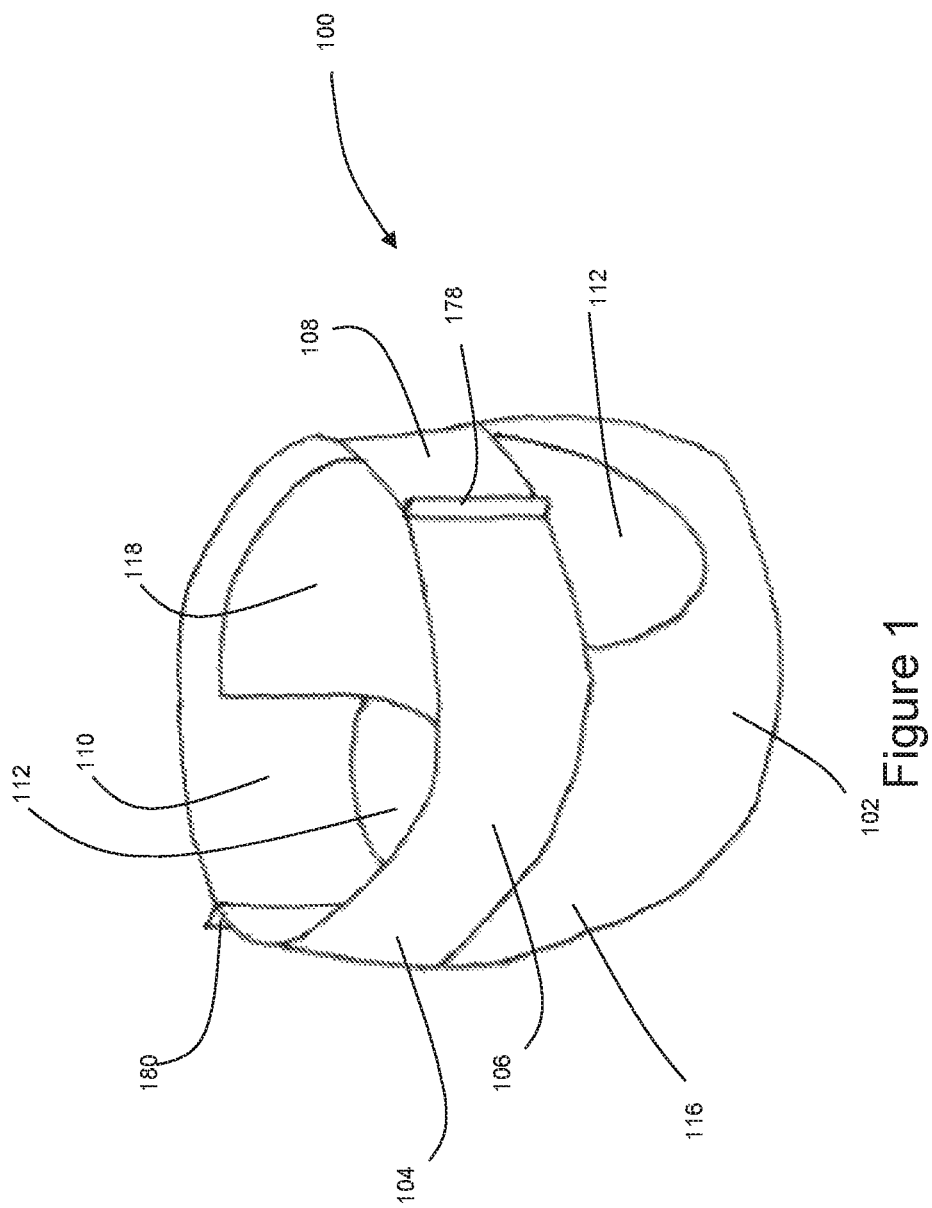
FIG. 1 is a perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer.

The present disclosure relates to methods for manufacturing absorbent articles, and in particular, to methods for making elastomeric laminates that may be used as components of absorbent articles. The elastomeric laminates may include a first substrate, a second substrate, and an elastic material located between the first substrate and second substrate. During the process of making the elastomeric laminate, one or more elastic strands may be advanced and stretched in a machine direction and may be joined with either or both the first and second substrates advancing the machine direction. The methods and apparatuses according to the present disclosure may be configured to automatically isolate elastic strands that may break during the assembly process. As discussed in more detail below, the apparatuses may include a snare member extending adjacent to and across a travel path of elastic materials in a converting process. More particularly, the snare member has an outer circumferential surface and defines a length defined between a first end portion and a second end portion. Thus, during the manufacture process, stretched elastics strands may advance past the snare member without contacting the outer circumferential surface of the snare member before being joined with a substrate. In the event that an elastic strand breaks, an upstream end portion of the elastic strand may retract back toward the snare member, wherein the upstream end portion wraps partially or completely around the outer circumferential surface of the snare member. Thus, the upstream end portion of the broken elastic strand is captured and isolated by the snare member. As discussed below, the outer circumferential surface of the snare member may be configured in various ways to help capture the broken elastic strand. For example, the outer circumferential surface of the snare member may include adhesive or other tacky substances. In other examples, tufts of bristles may extend outward from the outer circumferential surface of the snare member.

It is to be appreciated that the snare members may be configured in various ways and located in various positions along an assembly process to capture the retracting upstream end portions of broken elastic strands. For example, in some configurations, elastic strands may be configured to advance in a first direction to a first tangent point on an outer circumferential surface of a drum or roller. The elastic strands may also wrap along the outer circumferential surface of the drum such that the elastic strands extend from the first tangent point to a second tangent point on the outer circumferential surface of the drum. And the elastic strands advance in a second direction from the second tangent point on the outer circumferential surface of the drum. In some embodiments, the snare member may be positioned adjacent the drum, such that the snare member is positioned between the elastic strands and a plane extending through the second tangent point. In addition, the length of the snare member may extend in a third direction across the first direction of advancement of the elastic materials. Thus, in the event that an elastic strand breaks, an upstream end portion of a broken elastic strand retracts toward the drum and wraps along the outer circumferential surface of the snare member.

In some embodiments, a plurality of elastic strands may be configured to advance in a first direction to a drum so as to define a first strand transport plane. The plurality of elastic strands wrap along an outer circumferential surface of the drum and advance from the outer circumferential surface of the drum in a second direction so as to define a second strand transport plane. In turn, the snare member may be positioned adjacent the drum such that the length of the snare member extends in a third direction across the plurality of elastic strands advancing in first strand transport plane. In addition, the outer circumferential surface of the snare member may be positioned between the plurality of elastic strands and the second strand transport plane. Thus, in the event that an elastic strand breaks, an upstream end portion of a broken elastic strand retracts toward the drum and wraps along the outer circumferential surface of the snare member.

Thus, the snare member may help prevent loose ends of the broken strands from snapping back a significant distance toward an upstream portion of the manufacturing process. In some manufacturing configurations where several strands may advance in close proximity to one another, the snare members may help reduce the likelihood of a single broken strand causing adjacent elastic strands in the process to become broken. Further, snare members may also be placed in various locations along a manufacturing line as a troubleshooting tool to help more easily identify the specific causes of and/or locations where elastic strands are breaking.

As previously mentioned, the elastomeric laminates made according to the processes and apparatuses discussed herein may be used as to construct various types of components used in the manufacture of different types of absorbent articles. To help provide additional context to the subsequent discussion of the process embodiments, the following provides a general description of absorbent articles in the form of diapers that include components including the elastomeric laminates that may be produced with the methods and apparatuses disclosed herein.

FIGS. 1 and 2A show an example of a diaper pant 100 that may include components constructed from elastomeric laminates assembled in accordance with the apparatuses and methods disclosed herein. In particular, FIG. 1 shows a perspective view of a diaper pant 100 in a pre-fastened configuration, and FIG. 2A shows a plan view of the diaper pant 100 with the portion of the diaper that faces away from a wearer oriented towards the viewer. The diaper pant 100 shown in FIGS. 1 and 2A includes a chassis 102 and a ring-like elastic belt 104. As discussed below in more detail, a first elastic belt 106 and a second elastic belt 108 are connected together to form the ring-like elastic belt 104.

With continued reference to FIG. 2A, the chassis 102 includes a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The diaper 100 may also include a laterally extending front waist edge 120 in the front waist region 116 and a longitudinally opposing and laterally extending back waist edge 122 in the back waist region 118. To provide a frame of reference for the present discussion, the diaper 100 and chassis 102 of FIG. 2A is shown with a longitudinal axis 124 and a lateral axis 126. In some embodiments, the longitudinal axis 124 may extend through the front waist edge 120 and through the back waist edge 122. And the lateral axis 126 may extend through a first longitudinal or right side edge 128 and through a midpoint of a second longitudinal or left side edge 130 of the chassis 102.

As shown in FIGS. 1 and 2A, the diaper pant 100 may include an inner, body facing surface 132, and an outer, garment facing surface 134. The chassis 102 may include a backsheet 136 and a topsheet 138. The chassis 102 may also include an absorbent assembly 140 including an absorbent core 142 may be disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2A, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 120 in the front waist region 116 and the laterally extending back waist edge 122 in the back waist region 118. When the diaper pant 100 is worn on the lower torso of a wearer, the front waist edge 120 and the back waist edge 122 of the chassis 102 may encircle a portion of the waist of the wearer. At the same time, the chassis side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, allow the user of the diaper 100 including a chassis 102 having a particular size before extension to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2A, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; U.S. Patent Publication No. 2009/0312730A1; and U.S. patent application Ser. No. 13/435,503, entitled "METHODS AND APPARATUSES FOR MAKING LEG CUFFS FOR ABSORBENT ARTICLES", filed on Mar. 30, 2012.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1.

As previously mentioned, the ring-like elastic belt 104 is defined by a first elastic belt 106 connected with a second elastic belt 108. As shown in FIG. 2A, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2A, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 120 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2A, 3A, and 3B, the belt elastic material may include a plurality of elastic strands 168 which may be referred to herein as outer, waist elastics 170 and inner, waist elastics 172.

As shown in FIG. 2A, the outer, waist elastics 170 extend continuously laterally between the first and second opposing end regions 106a, 106b and across the central region 106c of the first elastic belt 106 and between the first and second opposing end regions 108a, 108b and across the central region 108c of the second elastic belt 108. In some embodiments, some elastic strands 168 may be configured with discontinuities in areas. For example, as shown in FIG. 2A, the inner, waist elastics 172 extend intermittently along the first and second elastic belts 106, 108. More particularly, the inner, waist elastics 172 extend along the first and second opposing end regions 106a, 106b and partially across the central region 106c of the first elastic belt 106. The inner, waist elastics 172 also extend along the first and second opposing end regions 108a, 108b and partially across the central region 108c of the second elastic belt 108. As such, the inner, waist elastics 172 do not extend across the entirety of the central regions 106c, 108c of the first and second elastic belts 106, 108. Thus, some elastic strands 168 may not extend continuously through regions of the first and second elastic belts 106, 108 where the first and second elastic belts 106, 108 overlap the absorbent assembly 140. In some embodiments, some elastic strands 168 may partially extend into regions of the first and second elastic belts 106, 108 where the first and second elastic belts 106, 108 overlap the absorbent assembly 140. In some embodiments, some elastic strands 168 may not extend into any region of the first and second elastic belts 106, 108 where the first and second elastic belts 106, 108 overlap the absorbent assembly 140. It is to be appreciated that the first and/or second elastic belts 106, 108 may be configured with various configurations of discontinuities in the outer, waist elastics 170 and/or the inner, waist elastic elastics 172.

In some embodiments, the elastic strands 168 may be disposed at a constant interval in the longitudinal direction. In other embodiments, the elastic strands 168 may be disposed at different intervals in the longitudinal direction. As discussed in more detail below, the belt elastic strands 168, in a stretched condition, may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt.

Figure 2B:
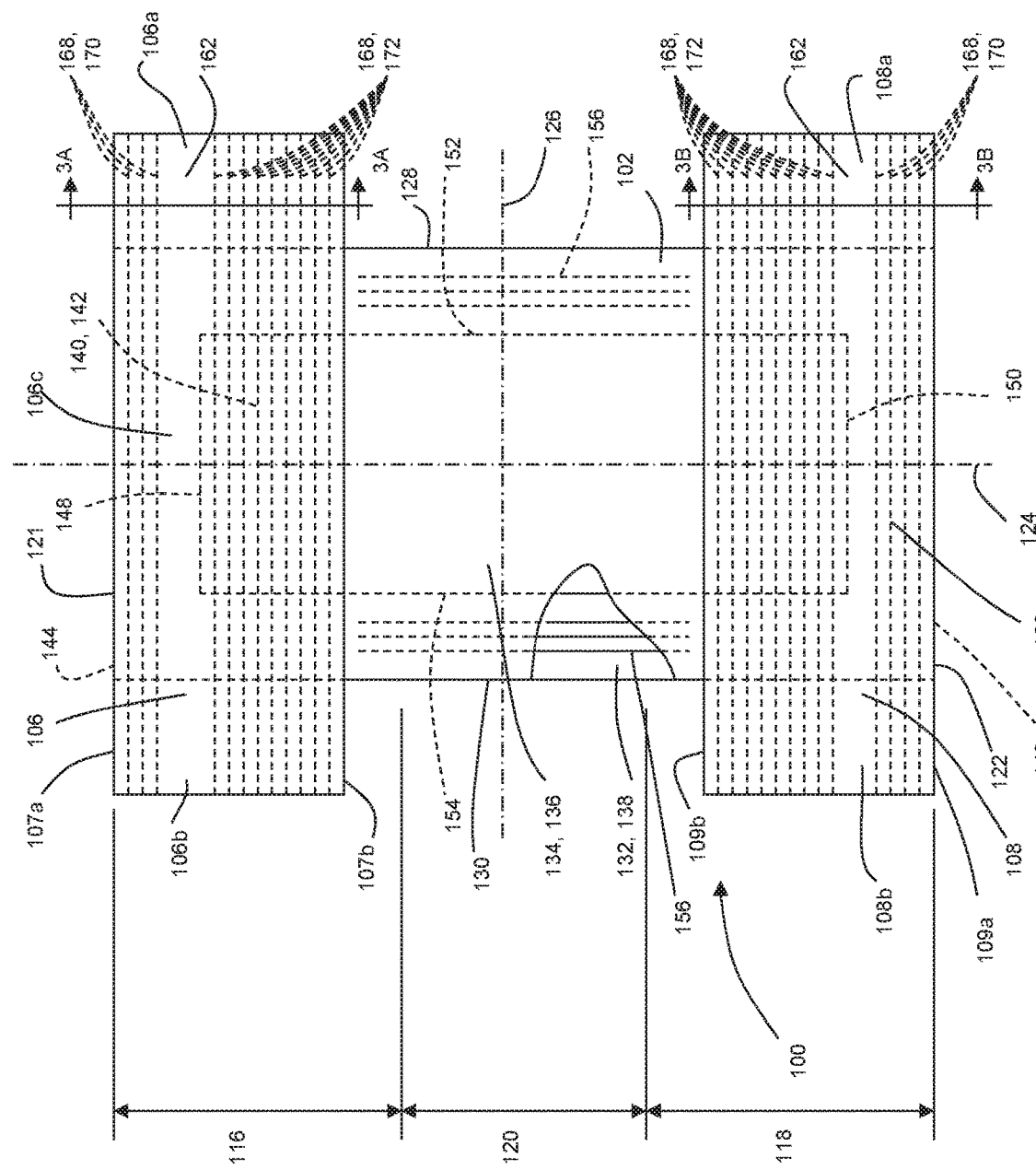
FIG. 2B is a partially cut away plan view of a second embodiment of a diaper pant.

It is to be appreciated that the chassis 102 and elastic belts 106, 108 may be configured in different ways other than as depicted in FIG. 2A. For example, FIG. 2B shows a plan view of a diaper pant 100 having the same components as described above with reference to FIG. 2A, except the first laterally extending end edge 144 of the chassis 102 is aligned along and coincides with the outer lateral edge 107*a* of the first elastic belt 106, and the second laterally extending end edge 146 is aligned along and coincides with the outer lateral edge 109*a* of the second belt 108.

Components of the disposable absorbent article (i.e., diaper, disposable pant, adult incontinence article, sanitary napkin, pantiliner, etc.) described in this specification can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases.

In at least one exemplary configuration, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

As previously mentioned, the apparatuses and methods according to the present disclosure may be utilized to assemble elastic laminates 302 used in various components of absorbent articles, such as for example, elastic belts 106, 108 and/or leg cuffs 156. Although the following methods may be provided in the context of the diaper 100 shown in FIGS. 1 and 2A, it is to be appreciated that the methods and apparatuses herein may be used to assemble various substrates and/or elastic laminates that can be used with various process configurations and/or absorbent articles, such as for example, disclosed in U.S. Pat. No. 7,569,039; U.S. Patent Publication Nos. US 2005/0107764A1, US 2012/0061016A1, and US 2012/0061015A1; U.S. patent application Ser. Nos. 13/434,984; 13/435,036; 13/435,063; 13/435,247; and 13/435,503, all filed on Mar. 30, 2012, all of which are incorporated by reference herein. For example, FIGS. 4A-6 show schematic views of a converting apparatus 300 adapted to manufacture elastomeric laminates 302.

As described in more detail below, the converting apparatus 300 shown in FIGS. 4A-6 operates to advance a continuous length of stretched elastic material 304, a continuous length of a first substrate 306, and a continuous length of a second substrate 308 along a machine direction MD. The apparatus 300 joins the stretched elastic material 304 with the first and second substrates 306, 308 to produce an elastomeric laminate 302. Although the elastic material 304 is illustrated and referred to herein as strands, it is to be appreciated that elastic material 304 may include one or more continuous lengths of elastic strands, ribbons, and/or films. The elastomeric laminates 302 can be used to construct various types of diaper components. For example, the elastomeric laminates 302 may be used as a continuous length of elastomeric belt material that may be converted into the first and second elastic belts 106, 108 discussed above with reference to FIGS. 1-3B. As such, the elastic strands 304 may correspond with the belt elastic material 168 interposed between the outer layer 162 and the inner layer 164, which in turn, may correspond with either the first and/or second substrates 306, 308. In other examples, the elastomeric laminates may used to construct waistbands in taped diaper configurations. Example taped diapers are disclosed in U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571. In yet other examples, the elastomeric laminates may be used to construct various types of leg cuff and/or topsheet configurations.

As discussed in more detail below, the converting apparatuses 300 may include metering devices arranged along a process machine direction MD, wherein the metering devices may be configured to advance and/or stretch the advancing elastic material and/or join stretched elastic material with one or more advancing substrates. It is to be appreciated that the relative placement of devices and movement of material is described as flowing in the machine direction through a process from upstream in the process to downstream in the process. As discussed below, the converting apparatuses may also include one or more broken strand isolator apparatuses arranged between metering devices. Each broken strand isolator apparatus may include one or more snare members. During operation, elastic material may advance in a first direction between a snare member and an upstream metering device. The elastic material extends or wraps along an outer circumferential surface of the upstream metering device. From the upstream metering device, the elastic material advances in a second direction to a downstream metering device. In the event that the stretched elastic material breaks while advancing from the upstream metering device to the downstream metering device, an upstream end portion of the broken elastic strand retracts in a direction that is opposite the second direction, toward upstream metering device and the broken strand isolator. In turn, the snare member captures the upstream end portion of the broken elastic strand, preventing the upstream end portion from retracting further upstream.

As shown in FIGS. 4A and 5A, a converting apparatus 300 for producing an elastic laminate 302 may include a first metering device 310, a second metering device 312, a third metering device 314, and a broken strand isolator apparatus 400. One or more continuous elastic strands 304 advance in a machine direction MD to the first metering device 310, wherein the elastic strands 304 wrap or extend along first metering device 310. The broken strand isolator device 400 is also positioned adjacent the first metering device 310 such that the elastic strands 304 advance between the broken strand isolator device 400 and the first metering device 310.

From the first metering device 310, the elastic strands 304 advance in the machine direction MD to the second metering device 312. Although the elastic strands 304 may advance onto the first metering device 310 in a stretched condition, it is to be appreciated that the apparatus 300 can be configured such that the elastic strands 304 may be stretched along the machine direction MD between the first metering device 310 and the second metering device 312. The stretched elastic strands 304 are also joined with a first substrate 306 at the second metering device 312. From the second metering device 312, the joined elastic strands 304 and first substrate 306 advance to the third metering device 314 and are joined with a second substrate 308 to produce an elastomeric laminate 302. It is to be appreciated that the apparatus 300 can be configured in various different ways. For example, the apparatus may be configured such that the elastic strands 304 are joined with the both the first and second substrates 306, 308 at the second metering device 312. It is also to be appreciated that different components may be used to construct the elastomeric laminates 302 in accordance with the methods and apparatuses herein. For example, the first and/or second substrates 306, 308 may include nonwovens and/or films. In addition, although FIGS. 4A and 5A show four elastic strands 304 advancing past a single isolator apparatus 400, it is to be appreciated that the apparatuses herein may be configured such that more or less than four elastic strands 304 advance through a single isolator apparatus 400, and/or that additional isolator apparatuses 400 may be arranged along the cross direction CD of a converting process and/or arranged along a machine direction MD in various different portions of a converting process.

As shown in FIGS. 4A and 5A, the first metering device 310 may include a first drum 315. It is to be appreciated that the first drum 315 may be configured as a stationary bar and may also be configured as a first roller 316 having an outer circumferential surface 318 and rotates about a first axis of rotation 320. The first roller 316 may be configured to rotate such that the outer circumferential surface 318 has a surface speed V1. The second metering device 312 may include a second drum 321. It is to be appreciated that the second drum 321 may be configured as a stationary bar and may also be configured as a second roller 322 having an outer circumferential surface 324 and rotates about a second axis of rotation 326. The second roller 322 may be configured to rotate such that the outer circumferential surface 324 has the same, or substantially the same, surface speed V1. In some embodiments, the second roller 322 may be configured to rotate such that the outer circumferential surface 324 has a surface speed that is greater than surface speed V1, and as such the elastic strands 304 may be stretched between the first and second metering devices 310, 312. With continued reference to FIG. 4A, the third metering device 314 may include a third drum 327. It is to be appreciated that the third drum 327 may be configured as a stationary bar and may also be configured as a third roller 328 having an outer circumferential surface 330 and rotates about a third axis of rotation 332. The third roller 328 may be configured to rotate such that the outer circumferential surface 330 has the same, or substantially the same, surface speed as the outer circumferential surface 324 of the second roller 322.

As shown in FIGS. 4A and 5A, the first substrate 306 includes a first surface 338 and an opposing second surface 340, and the first substrate 306 advances at speed V1 in the machine direction MD to the second roller 322. In particular, the first substrate 306 advances in the machine direction MD at speed V1 to the second roller 322 where the first substrate 306 partially wraps around the outer circumferential surface 324 of the second roller 322. From the second roller 322, the first substrate 306 advances to the third roller 328. As such, the second surface 340 of the first substrate 306 travels in the same direction as and in contact with the outer circumferential surface 324 of the second roller 322. In addition, the second substrate 308 includes a first surface 342 and an opposing second surface 344, and the second substrate 308 advances at speed V1 in the machine direction MD to the third roller 328. In particular, the second substrate 308 advances in the machine direction MD at speed V1 to the third roller 328 where the second substrate 308 partially wraps around the outer circumferential surface 330 of the third roller 328. As such, the first surface 342 of the second substrate 308 travels in the same direction as and in contact with the outer circumferential surface 330 of the third roller 328.

With continued reference to FIGS. 4A and 5A, the elastic strands 304 advance in the machine direction MD to the first metering device 310, which may be configured as the first drum 315 or first roller 316. Upstream of the first metering device 310, the elastic strands 304 may advance at speed V1 or less. The elastics strands 304 contact, extend, and wrap along the outer circumferential surface 318 of the first roller 316. From the first roller 316, the elastic strands 304 advance to the second roller 322 where the elastic strands 304 are joined with the first substrate 306. As previously mentioned, the elastic strands 304 may be stretched before advancing to the first roller 316. In addition, the elastic strands 304 may be stretched between the first roller 316 and the second roller 322. As such, the elastics strands 304 may be joined with the first surface 338 of the first substrate 306 on the second roller 322. In turn, the joined stretched elastic strands 304 and first substrate 306 advance from second roller 322 to the third roller 328, wherein the elastic strands 304 and first substrate 306 are joined with the second substrate 308. In particular, the elastic strands 304 are positioned between the first and second substrates 306, 308 such that the elastic material is joined with the first surface 338 of the first substrate 306 and the second surface 344 of the second substrate 308 to produce a continuous length of elastomeric laminate 302. As shown in FIG. 4A, the elastic strands 304 may advance past an adhesive applicator device 334 that applies adhesive 336 to the elastic strands 304 before advancing to the second nip 356. It is to be appreciated that adhesive may also be applied to the first surface 338 of the first substrate 306 before and/or while being joined with the elastic strands 304 and/or the second substrate 308. In addition, it is to be appreciated that adhesive may be applied to the second surface 344 of the second substrate 308 before or while being joined with the elastic strands 304 and first substrate 306.

Figure 6:
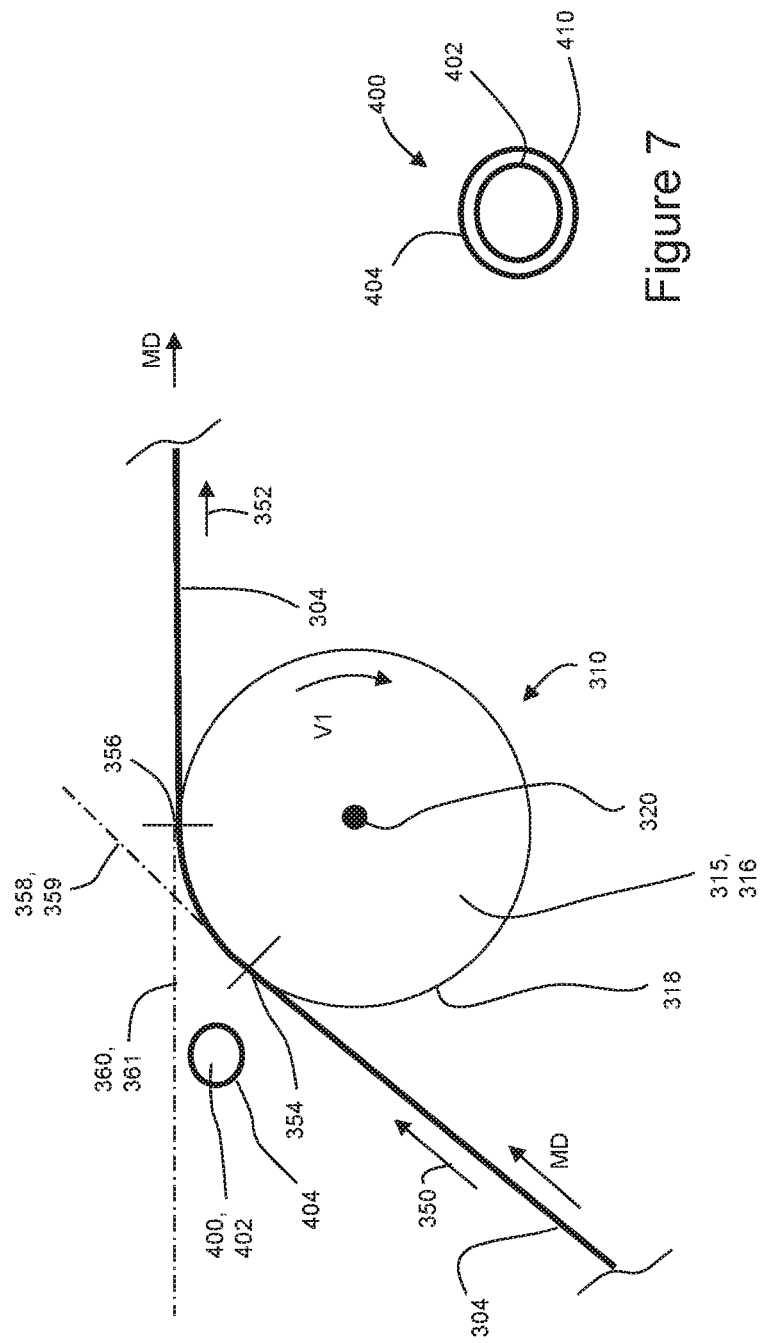
FIG. 6 is a detailed view of the elastic strands, first drum, and snare member of FIG. 4A.

As previously mentioned, some elastic strands 304 may break while the apparatus 300 is producing an elastomeric laminate 302. FIGS. 4A-5D illustrate a sequence wherein a single elastic strand 304 breaks and is captured by the isolator apparatus 400. As described above, FIGS. 4A and 5A shows the apparatus 300 operating to produce an elastomeric laminate 302 with four stretched elastic strands 304 advancing between the isolator apparatus 400 and the first metering device 310. The elastic strands also advance from the first metering device 310 to the second metering device 312. As shown in FIG. 4A, the elastic strands 304 advance in a first direction 350 to the first drum 315 or first roller 316. The elastic strands 304 also extend or wrap along the outer circumferential surface 318 of the first roller 316. And from the outer circumferential surface 318 of the first roller 316, the elastic strands 304 advance in a second direction 352 to the second metering device 312. With particular reference to FIGS. 4A and 6, the elastic strands 304 advance in the first direction 350 to and make contact with the outer circumferential surface 318 at a first tangent point 354 on the outer circumferential surface 318 on the first drum 315 or first roller 316. The elastic strands 304 extend or wrap along the outer circumferential surface 318 of the first drum 315 or roller 316 to a second tangent point 356. From the second tangent point 356, the elastic strands 304 advance from the outer circumferential surface 318 of the first drum 315 or roller 316 in a second direction 352. FIG. 6 also shows a first plane 358 that is tangent to the outer circumferential surface 318 of the first drum 315 or roller 316 and extends through the first tangent point 354, and a second plane 360 that is tangent to the outer circumferential surface 318 of the first drum 315 or roller 316 and extends through the second tangent point 356. A plurality of elastic strands 304 aligned in the cross direction CD and advancing in the first direction 350 may also define a first strand transport plane 359 that is coincident with the first plane 358. And a plurality of elastic strands 304 aligned in the cross direction CD and advancing in the second direction 352 may also define a second strand transport plane 361 that is coincident with the second plane 360.

With continued reference to FIGS. 4A, 5A, and 6, the isolator apparatus 400 includes a snare member 402 positioned adjacent the first drum 315 or roll 316, such that the elastic strands 304 advance between the snare member 402 and the first drum 315 or roll 316. More particularly, the snare member includes an outer circumferential surface 404 and defines a length between a first end portion 406 and a second end portion 408, wherein the length of the snare member 402 extends in a cross direction CD or third direction 362 across the plurality of elastic strands 304. It is to be appreciated that the third direction 362 may or may not be perpendicular to the first direction 350. In some embodiments, the snare member 402 may be positioned such that the elastic strands 304 are between the outer circumferential surface 404 of the snare member 402 and the outer circumferential surface 318 of the first drum 315 or roller 316. It is to be appreciated that the snare member 402 may be positioned in various locations upstream of the second tangent point 356. For example, the snare member 402 may be positioned upstream of the second tangent point 356, and positioned between the strands 304 and the second plane 360 (and/or the second strand transport plane 361). In some embodiments, the snare member 402 may be positioned upstream of the second tangent point 356, and positioned between the strands 304 and the second plane 360 (and/or the second strand transport plane 361), as well as positioned between the first plane 358 (and/or the first strand transport plane 359) and the second plane 360 (and/or the second strand transport plane 361). In some embodiments, the snare member 402 is positioned such that the outer circumferential surface 404 does not contact the elastic strands 304 and/or the second plane 360 (and/or the second strand transport plane 361). In some embodiments, the snare member 402 is positioned such that the first plane 358 (and/or the first strand transport plane 359) intersects the outer circumferential surface 404 of the snare member 402, whereas the snare member 402 is also positioned such that the outer circumferential surface 404 does not contact the elastic strands 304 and/or the second plane 360 (and/or the second strand transport plane 361).

Referring now to FIGS. 4B and 5B, an operating state is shown wherein one of the elastic strands 304 has broken or separated in the machine direction MD between the first metering device 310 and the second metering device 312, thus creating an upstream end portion 346 and a downstream end portion 348. Because the elastic strands 304 are stretched, the downstream end portion 348 may snap back in a downstream direction or the second direction 352 toward the second roller 322, and the upstream end portion 346 may snap back in an upstream direction or a fourth direction 364 toward the first roller 316 and the isolator apparatus 400. And as shown in FIGS. 4B-5B, the upstream end portion 346 of the broken elastic strand 304 snaps back in the fourth direction 364 that is opposite the second direction 352 and toward the isolator apparatus 400. As shown in FIGS. 4B-5C, the downstream end portion 348 of the broken elastic strand 304 continues to advance in the machine direction MD to be incorporated into the elastomeric laminate 302.

As previously mentioned, the upstream end portion 346 of the broken elastic strand 304 snaps back in a direction toward the first drum 315 or roller 316 and becomes captured by the isolator apparatus 400, such as shown in FIGS. 4B-5D. With reference to FIGS. 4C and 5C, the upstream end portion 346 snaps back and contacts the outer circumferential surface 404 of the snare member 402. The upstream end portion 346 may also wrap partially or entirely around the outer circumferential surface 404 of the snare member 402, such as shown in FIGS. 4D and 5D. In turn, the wrapped upstream end portion 346 of the broken elastic strand 304 on the snare member 402 is captured and isolated by the snare member 402, thus preventing loose ends of broken strands from snapping back a significant distance toward an upstream portion of the manufacturing process.

Figure 7:
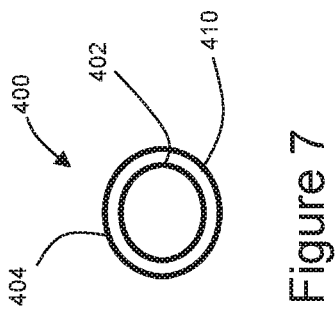
FIG. 7 is a side view of a second embodiment of a snare member.
Figure 8:
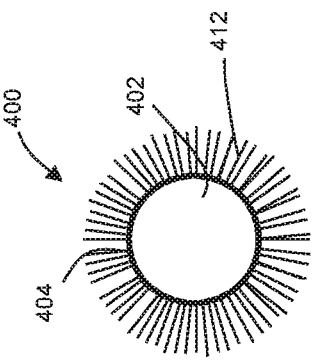
FIG. 8 is a side view of a third embodiment of a snare member.

It is to be appreciated that the isolator apparatuses 400 herein may be configured in various different ways to capture upstream end portions of broken elastic material. In some configurations, the outer circumferential surface 404 of the snare member 402 is configured to increase the frictional engagement between the upstream end portion 346 of the broken elastic strand 304 and the outer circumferential surface 404. For example, the outer circumferential surface 404 of the snare member 402 may be coated with an adhesive or other tacky substance that helps to grab and/or hold the upstream end portion 346 of the broken elastic strand 304 onto the snare member 402. For example, adhesives may be applied directly to the outer circumferential surface 404. In some examples, adhesive tape may be joined with the outer circumferential surface 404 of the snare member 402 such that a tacky surface of the tape is exposed to the upstream end portion 346 of the broken elastic strand 304. In another example, the outer circumferential surface 404 of the snare member 402 may be knurled. In yet another example, the snare member 402 may be configured with an outer sleeve 410 defining the outer circumferential surface 404 that includes a tacky substance, wherein the outer sleeve 410 may facilitate ease of removal and/or replacement, such as shown in FIG. 7. In some embodiments, the snare member 402 may include bristles 412 extending outward from the outer circumferential surface 404, such as shown in FIG. 8. In the arrangement of FIG. 8, the retracting upstream end portion 346 of the broken elastic strand 304 may be captured by becoming entangled in the bristles 412. It is also be to be appreciated that the snare member 402 can be configured with various different shaped cross sections. For example, the figures herein show the snare member 402 as having a circular cross section. In some embodiments, the snare member 402 may be configured with a rectangular, square, triangular, elliptical, oval, or cross sections corresponding with other geometric shapes. In some embodiments, the snare member 402 may be configured as a flat plate with tacky and/or roughened surfaces. It is also to be appreciated that the snare member 402 may extend in a straight line and/or curved lines across the elastic strands 304.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for isolating broken strands of elastic, the method comprising steps of:

advancing an elastic strand in a first direction to a first tangent point on an outer circumferential surface of a drum;

wrapping the elastic strand along the outer circumferential surface of the drum, wherein the elastic strand extends from the first tangent point to a second tangent point on the outer circumferential surface of the drum;

advancing the elastic strand from the second tangent point on the outer circumferential surface of the drum in a second direction;

positioning a snare member adjacent the drum, wherein the snare member has an outer circumferential surface and defines a length defined between a first end portion and a second end portion, wherein the length of the snare member extends in a third direction across the first direction of advancement of the elastic strand, and wherein the snare member is positioned between the elastic strand and a plane extending through the second tangent point;

separating the elastic strand in the second direction to create an upstream end portion and a downstream end portion;

retracting the upstream end portion toward the drum; and wrapping the upstream end portion along the outer circumferential surface of the snare member.

2. The method of claim 1, further comprising a step of rotating the drum.

3. The method of claim 1, wherein the snare member defines a circular cross section.

4. The method of claim 1, further comprising a step of applying adhesive to the outer circumferential surface of the snare member.

5. The method of claim 1, wherein the third direction is perpendicular to the first direction.

6. The method of claim 1, further comprising a step of stretching the elastic strand.

* * * * *